(12) United States Patent
Nagai et al.

(10) Patent No.: US 7,531,657 B2
(45) Date of Patent: May 12, 2009

(54) METHOD FOR PREPARING SULPHOSTIN AND ANALOGUE THEREOF OR PREPARATION INTERMEDIATE THEREOF

(75) Inventors: Masashi Nagai, Nishitokyo (JP); Hiroko Yamazaki, Tokyo (JP); Keiichirou Yamamoto, Tokyo (JP); Masatoshi Abe, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 975 days.

(21) Appl. No.: 10/498,272

(22) PCT Filed: Dec. 16, 2002

(86) PCT No.: PCT/JP02/13140

§ 371 (c)(1), (2), (4) Date: Jun. 8, 2004

(87) PCT Pub. No.: WO03/051895

PCT Pub. Date: Jun. 26, 2003

(65) Prior Publication Data

US 2005/0020834 A1 Jan. 27, 2005

(30) Foreign Application Priority Data

Dec. 17, 2001 (JP) ............................. 2001-382818
Dec. 17, 2001 (JP) ............................. 2001-382862
Nov. 13, 2002 (JP) ............................. 2002-329474

(51) Int. Cl.
C07F 9/00 (2006.01)
C07F 9/02 (2006.01)
C07D 205/08 (2006.01)
C07D 223/12 (2006.01)

(52) U.S. Cl. ..................... 546/21; 548/412; 549/363; 549/528

(58) Field of Classification Search ................ 546/21; 548/412; 540/363, 528
See application file for complete search history.

(56) References Cited

U.S. PATENT DOCUMENTS 6,579,989 B1 * 6/2003 Takeuchi et al. ............ 548/412

FOREIGN PATENT DOCUMENTS

| EP | 1 043 328 | 10/2000 |
|---|---|---|
| EP | 1 184 388 | 3/2002 |
| JP | 2000-327689 | 11/2000 |
| WO | 99/25719 | 5/1999 |
| WO | 00/69868 | 11/2000 |
| WO | 02/055088 | 7/2002 |

OTHER PUBLICATIONS

Curran, Angew Chem. Int. Ed. vol. 37 pp. 1174-1196 (1998).*

* cited by examiner

Primary Examiner—Janet L. Andres
Assistant Examiner—Raymond Covington
(74) Attorney, Agent, or Firm—Nields, Lemack & Frame, LLC

(57) ABSTRACT

A method for preparing a compound represented by the following general formula (5)

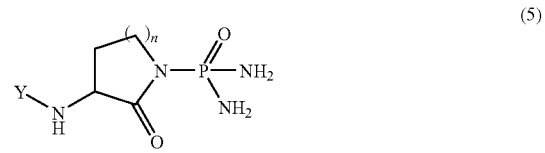

(5)

where, n is an integer of 0 to 3; and Y represents a protecting group for an amino group, the method including the steps of reacting a compound represented by the following general formula (3)

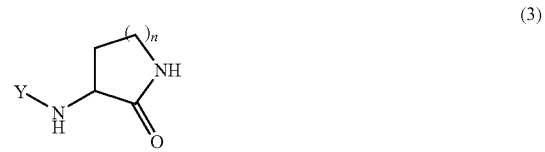

(3)

where n and Y are as described above, with a silylating agent, and subsequently reacting it with P (=O) $T_3$, where T represents a halogen atom, and further with ammonia.

A method for preparing an optically active intermediate of sulphostin or an analogue thereof, which is an optically active amine salt of an optically active compound represented by the following general formula (8)

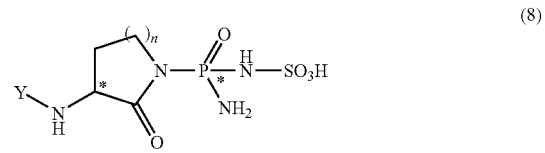

(8)

where n is integer of 0 to 3; Y represents protecting group for the amino group; and each configuration at C* and P* may be the same or different and indicates S or R, the method including reacting a compound represented by the following general formula (7)

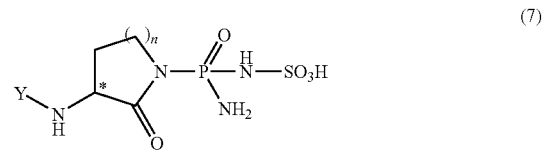

(7)

where n and Y are as described above; and the configuration of C* indicates either of S or R, with an optically active amine, and resolving the formed diastereomeric salt by fractional crystallization.

18 Claims, No Drawings

METHOD FOR PREPARING SULPHOSTIN AND ANALOGUE THEREOF OR PREPARATION INTERMEDIATE THEREOF

TECHNICAL FIELD

The present invention relates to a new method for preparing sulphostin, a physiologically active substance, an analogue thereof and a preparation intermediate thereof.

BACKGROUND ART

Sulphostin and analogues of sulphostin represented by the following general formula (1) (where n is an integer of 0 to 3) are new organic compounds having a dipeptidyl peptidase IV inhibitory action. In particular, a compound represented by the following general formula (2) having the structure in which, in the general formula (1), n is 2, the configuration at C* is S, the configuration at P* is R, is described as sulphostin in the following literature.

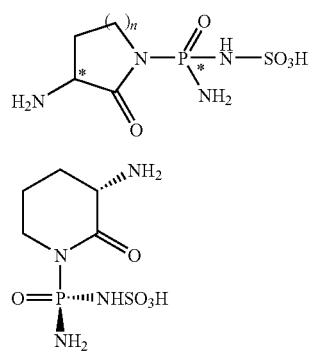

These compounds are expected to be applied to medicines, such as an immunomodulator, a hormone regulator, an anti-HIV drug, an antiallergic drug, an antiinflammatory drug and an antirheumatic drug (WO99/25719).

In addition, as for preparation of the above compound, because a fermentation method has low productivity and is not suitable for mass production for the present, a preparation method by synthesis is reported (JP-A-2000-327689). The preparation method employs a process of activating an amide with the use of a super strong base under ultra low temperature (−78°C.) conditions, and then reacting phosphonyl chloride and liquid ammonia under similar temperature conditions, in the step of preparing phosphoric acid amide. In the step of resolution, chromatography is used, so that the resolution is imperfect thus making it difficult to provide a product of high purity. Accordingly, the above preparation method cannot produce a large amount of the above compound in an industrial scale.

DISCLOSURE OF THE INVENTION

The present invention provides a new method for preparing a preparation intermediate of sulphostin and an analogue of sulphostin by a mild and easy operation, which aims at mass production which has been difficult according to the prior art.

In addition, the present invention provides a new method for preparing an optically active intermediate, which aims at mass production of sulphostin and analogues thereof having a high optical purity, which has been conventionally difficult.

The present inventors has made an extensive investigate, and found a method for preparing the compounds represented by the following general formula (5) at a high yield under more moderate and milder conditions than those in the prior art, by silylating a compound represented by the general formula (3) in a mild condition at first, and then reacting it with a phosphorus oxyhalide represented by the general formula (4) and ammonia. Secondly, the present inventors found a method of sulfonating the compound represented by the general formula (5'), then reacting the resulting compound represented by the general formula (7) with an optically active amine and fractionating the resulting diastereomer salt by fractional crystallization, to obtain an optically active amine salt of an optically active substance represented by the general formula (8). The present inventors then obtained sulphostin and the analogues thereof represented by the general formula (1) by subsequently removing a protecting group for an amino group and an optically active amine by a conventional process. Thus, the inventors found a new selection method for obtaining sulphostin and the analogues thereof represented by the general formula (1) from compounds represented by the general formula (3), and completed the present invention.

More specifically, the present invention relates to the following (i) to (xxv).

(i) A method for preparing a compound represented by the following general formula (5)

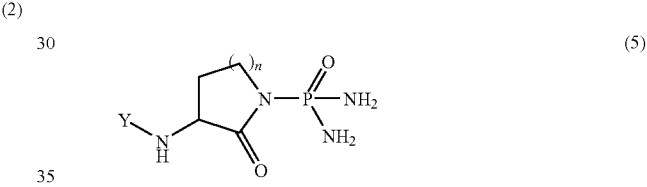

where n is an integer of 0 to 3; and Y represents a protecting group for an amino group, comprising the steps of reacting a compound represented by the following general formula (3)

where n and Y are as described above, with a silylating agent, and subsequently reacting it with a phosphorus oxyhalide represented by the general formula (4)

$$P(=O)T_3 \quad (4)$$

where T is a halogen atom and further with ammonia.

(ii) The preparation method according to the above (i), wherein the above described Y is a protecting group of a carbamate type or an amide type.

(iii) The preparation method according to the above (ii), wherein the above described Y is a benzyloxycarbonyl group or a tert-butoxycarbonyl group optionally substituted; and n is 2.

(iv) The preparation method according to any one of the above (i) to (iii), wherein the compound represented by the above described general formula (3) is an optically active substance.

(v) The preparation method according to any one of the above (i) to (iv), wherein T is a chlorine atom in the above described general formula (4).
(vi) The preparation method according to any one of the above (i) to (v), wherein the above described silylating agent is represented by the following general formula (6)

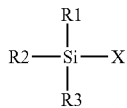
(6)

where R1, R2 and R3 each independently represent a lower alkyl group or an aryl group; and X represents a halogen atom or a fluorinated alkyl sulfonate.
(vii) The preparation method according to the above (vi), wherein the above described silylating agent is trimethylsilyl chloride.
(viii) The preparation method according to any one of the above (i) to (vii), wherein a reaction temperature is −20 to 80° C. in the steps of preparing a compound represented by the general formula (5) from a compound represented by the above described general formula (3).
(ix) A method for preparing an optically active intermediate of optically active sulphostin or analogues thereof, which is an optically active amine salt of an optically active compound represented by the following general formula (8)

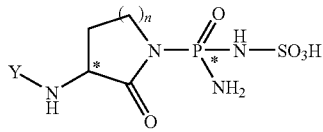
(8)

where n is an integer of 0 to 3; Y represents a protecting group for the amino group; and each configuration at C* and P* may be the same or different and indicates S or R, comprising the steps of reacting a compound represented by the following general formula (7)

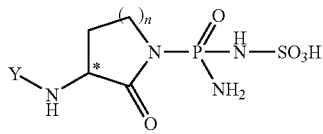
(7)

where n and Y are as described above; and the configuration of C* indicates either S or R, with an optically active amine, and resolving a formed diastereomeric salt by fractional crystallization.
(x) A method for preparing an optically active sulphostin or analogues thereof represented by the following general formula (1)

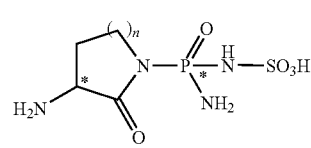
(1)

where n is an integer of 0 to 3; and each configuration of C* and P* may be the same or different and indicates S or R, comprising the steps of reacting a compound represented by the following general formula (7)

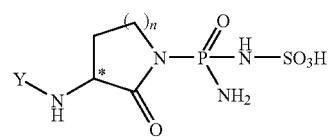
(7)

where n is an integer of 0 to 3, Y represents a protecting group for an amino group, and a configuration of C* indicates either of S or R, with an optically active amine, resolving a formed diastereomeric salt by fractional crystallization to obtain an optically active amine salt of an optically active compound represented by the following general formula (8)

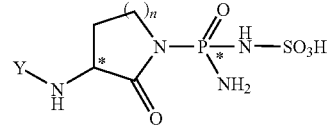
(8)

(where n is an integer of 0 to 3, Y represents the protecting group of the amino group; n, C* and P* are the same meanings as above), and then removing the protecting group for the amino group and the optically active amine by a conventional process.
(xi) The method according to the above (ix) or (x), wherein the optically active amine is represented by the following general formula (9)

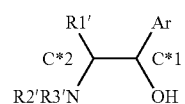
(9)

where Ar represents a phenyl group which may have a substituent group; R1' represents a lower alkyl group which may have a substituent group or an aryl group which may have a substituent group; each of R2' and R3' may be the same or different and represents a hydrogen atom or a lower alkyl group; each configuration of C*1 and C*2 may be the same or different and indicates S or R.
(xii) The method according to the above (ix) or (x), wherein the above described optically active amine is a compound selected from the group consisting of (1R,2S)-(−)-2-amino-1,2-diphenylethanol, (1S,2R)-(+)-2-amino-1,2-diphenylethanol, (1R,2S)-(−)-ephedrine, (1S,2R)-(+)- ephedrine, (1R,2S)-(−)-N-methylephedrine, (1S,2R)-(+)-N-methylephedrine, (1R,2S)-(−)-4-hydroxyephedrine, (1S,2R)-(+)-4-hydroxyephedrine, (1R,2S)-(−)-norephedrine, (1S,2R)-(+)-norephedrine, (1R,2S)-(−)-3,4-dihydroxynorephedrine, (1S,2R)-(+)-3,4-dihydroxynorephedrine, (1S,2R)-(−)-2-dibutylamino-1-phenyl-1-propanol, (1R,2S)-(+)-2-dibutylamino-1-phenyl-1-propanol, (1S,2S)-(+)-pseudoephedrine, (1R,2R)-(−)-pseudoephedrine, (1S,2S)-(+)-N-methylpseudoephedrine, (1R,2R)-(−)-N-methylpseudoephedrine, (1S,2S)-(+)-2-amino-3-methoxy-1-phenyl-1-propanol, (1R,2R)-(−)-2-amino-3-methoxy-1-phenyl-1-propanol, erythro-1,2-diphenyl-2-(propylamino)ethanol, erythro-2-(isopropylamino)-1,2-diphenylethanol, (1R,2R)-(−)-2-amino-1-phenyl-1,3-propanediol, (1S,2S)-(+)-2-amino-1-phenyl-1,3-propanediol, (1R,2R)-(−)-2-amino-1-(4-nitrophenyl)-1,3-propanediol and (1S,2S)-(+)-2-amino-1-(4-nitrophenyl)-1,3-propanediol.

(xiii) The method according to the above (ix) or (x), wherein the above described optically active amine is a compound selected from the group consisting of (1R,2S)-(−)-2-amino-1,2-diphenylethanol, (1S,2R)-(+)-2-amino-1,2-diphenylethanol, (1R,2S)-(−)-ephedrine, (1S,2R)-(+)-ephedrine, (1R,2S)-(−)-N-methylephedrine, (1S,2R)-(+)-N-methylephedrine, (1R,2S)-(−)-4-hydroxyephedrine, (1S,2R)-(+)-4-hydroxyephedrine, (1R,2S)-(−)-norephedrine, (1S,2R)-(+)-norephedrine, (1R,2S)-(−)-3,4-dihydroxynorephedrine, (1S,2R)-(+)-3, 4-dihydroxynorephedrine, (1S,2R)-(−)-2-dibutylamino-1-phenyl-1-propanol and (1R,2S)-(+)-2-dibutylamino-1-phenyl-1-propanol.

(xiv) The method according to the above (ix) or (x), wherein the above described optically active amine is (1R,2S)-(−)-2-amino-1,2-diphenylethanol or (1S,2R)-(+)-2-amino-1,2-diphenylethanol.

(xv) The method according to any one of the above (ix) to (xiv), wherein Y in the above general formula (7) is a protecting group of a carbamate type or an amide type.

(xvi) The method according to any one of the above (ix) to (xiv), wherein Y in the above described general formula (7) is a benzyloxycarbonyl group or a tert-butoxycarbonyl group that may have a substituent group; and n is 2.

(xvii) The method according to any one of the above (ix) to (xiv), wherein Y in the general formula (7) is an unsubstituted benzyloxycarbonyl group; and n is 2.

(xviii) The method according to any one of the above (ix) to (xvii), wherein the compound having the configuration of S at C* and the configuration of S at P* in the above described general formula (8) is obtained by reacting 1 mol of a compound having the configuration of S at C* in the above general formula (7), with 0.2 to 1.4 mol equivalent of the optically active amine having the configuration of S at C*1 and the configuration of R at C*2 in the above described general formula (9), as a hardly soluble salt consisting of 1 part of itself and 1 part of the above optically active amine.

(xix) The method according to any one of the above (ix) to (xvii), wherein the compound having the configuration of S at C* and the configuration of R at P* in the above described general formula (8) is obtained by reacting 1 mol of a compound having the configuration of S at C* in the above described general formula (7), with 1.5 to 10.0 mol equivalent of an optically active amine having the configuration of S at C*1 and the configuration of R at C*2 in the above described general formula (9), as a hardly soluble salt consisting of 1 part of itself and 2 part of the above optically active amine.

(xx) The method according to any one of the above (ix) to (xvii), wherein the compound having the configuration of R at C* and the configuration of R at P* in the above described general formula (8) is obtained by reacting 1 mol of a compound having the configuration of R at C* in the above described general formula (7), with 0.2 to 1.4 mol equivalent of an optically active amine having the configuration of R at C*1 and the configuration of S at C*2 in the above described general formula (9), as a hardly soluble salt consisting of 1 part of itself and 1 part of the above optically active amine.

(xxi) The method according to any one of the above (ix) to (xvii), wherein the compound having the configuration of R at C* and the configuration of S at P* in the above described general formula (8) is obtained by reacting 1 mol of a compound having the configuration of R at C* in the above described general formula (7), with 1.5 to 10.0 mol equivalent of an optically active amine having the configuration of R at C*1 and the configuration of S at C*2 in the above described general formula (9), as a hardly soluble salt consisting of 1 part of itself and 2 part of the above optically active amine.

(xxii) The method according to the above (ix), wherein the optically active amine salt of an optically active substance represented by the following general formula (8)

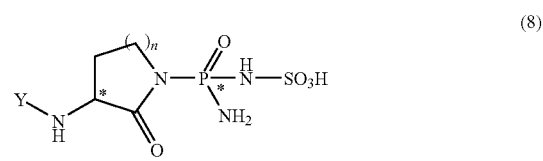

where n is an integer of 0 to 3; Y represents a protecting group for the amino group; and each configuration at C* and P* may be the same or different and indicates S or R, is obtained by sulfonating a compound represented by the following general formula (5')

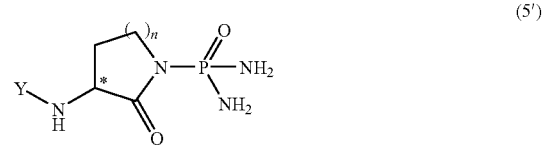

where n and Y are as described above; and the configuration at C* indicates S or R, by sulfur trioxide, reacting the resulting compound represented by the general formula (7) with an optically active amine without isolating it, and resolving a formed diastereomeric salt with a fractional crystalliation process.

(xxiii) The preparation method according to any one of (i), (ix), (x) and (xxii), wherein the optically active sulphostin or the analogue thereof represented by the following general formula (1)

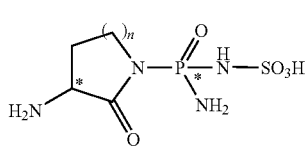

(1)

where n is an integer of 0 to 3; each configuration at C* and P* may be the same or different and indicates S or R, is obtained by reacting a compound represented by the following general formula (3')

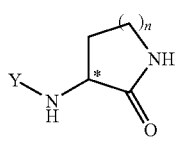

(3')

where n is an integer of 0 to 3, Y represents a protecting group for the amino group, and the configuration at C* indicates S or R, sequentially with a sililating agent, with a phosphorus oxyhalide represented by the general formula (4)

 (4)

where T represents a halogen atom, and further with ammonia; sulfonating the resulting compound represented by the following general formula (5')

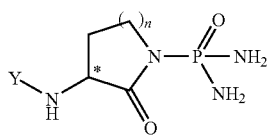

(5')

where n, Y and C* are as described above, with sulfur trioxide; reacting the resulting compound represented by the general formula (7) with an optically active amine, without isolating it; resolving a formed diastereomeric salt with a fractional crystallization process to obtain an optically active amine salt of an optically active substance represented by the following general formula (8)

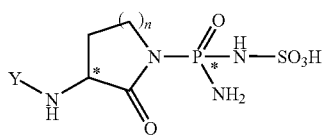

(8)

where n and Y are as described above; and C* and P* have the same meanings as above); and then removing the protecting group of the amino group and the optically active amine with a conventional process.

(xxiv) A salt of an optically active compound represented by the following general formula (8)

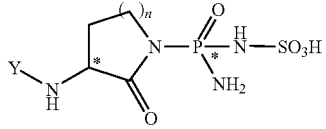

(8)

where n is an integer of 0 to 3; Y represents a protecting group for the amino group; and each configuration at C* and P* may be the same or different and indicates S or R, with an optically active amine represented by the following general formula (9)

(9)

where Ar represents a phenyl group which may have a substituent group; R1' represents a lower alkyl group which may have a substituent group, or an aryl group which may have a substituent group; each of R2' and R3' may be the same or different and represents a hydrogen atom or a lower alkyl group; and each configuration at C*1 and C*2 may be the same or different and indicates S or R.

(xxv) The salt according to the above (xxiv), wherein the above described optically active amine is (1R,2S)-(−)-2-amino-1,2-diphenylethanol or (1S,2R)-(+)-2-amino-1,2-diphenylethanol.

BEST MODE FOR CARRYING OUT THE INVENTION

The preparation method of the present invention is described below.

In the present invention, a lower alkyl group means a saturated hydrocarbon group having a straight chain or a branched chain having 1 to 10 carbon atoms; includes, for instance, a methyl group, an ethyl group, an n-propyl group, an n-butyl group, an n-pentyl group, an n-hexyl group, an isopropyl group, a sec-butyl group and a tert-butyl group; and preferably includes an alkyl group having 1 to 5 carbon atoms.

In the present invention, an aryl group means an aromatic hydrocarbon group having 6 to 10 carbon atoms, and includes, for instance, a phenyl group and a naphthyl group.

In the phenyl group which may have a substituent group, the aryl group which may have a substituent group and a benzyloxycarbonyl group which may have a substituent group, the number of substituent groups may be, for instance, 1 to 5, and each of several substituent groups may be the same or different. The substituent groups include a substituent group selected from the group consisting of an alkyl group having 1 to 5 carbon atoms, an alkenyl group having 2 to 5 carbon atoms, a cycloalkyl group having 3 to 6 carbon atoms, an alkoxyl group having 1 to 5 carbon atoms, an acyl group having 1 to 5 carbon atoms, an acyloxy group having 1 to 5 carbon atoms, an acylamino group having 1 to 5 carbon atoms, a halogenoalkyl group having 1 to 3 carbon atoms, a hydroxyl group, a cyano group, a nitro group and a halogen atom.

The substituent group in the lower alkyl group which may have a substituent group includes the above-mentioned groups in the phenyl group which may have the substituent groups, in the aryl group which may have the substituent group, and in the benzyloxycarbonyl group which may have the substituent group.

Compounds represented by the general formula (3), which are raw materials in the preparation method of the present invention, can be prepared by the method according to JP-A-2000-327689.

The protecting group Y in the compound represented by the general formula (3) may be any protecting group for the amino group used in a normal organic synthesis or the like, and includes, for instance, but is not particularly limited to, a protecting group of a carbamate type such as a benzyloxycarbonyl group which may have a substituent group (when having the substituent groups in the benzene ring, there may be, for instance, one to five substituent groups being as described above), and a tert-butoxycarbonyl group; and a protecting group of an amide type such as a formyl group, an acetyl group and a trifluoroacetyl group. The protecting group preferably includes a protecting group of the carbamate type or the amide type, more preferably a benzyloxycarbonyl group which may have the substituent group or a tert-butoxycarbonyl group, and most preferably an unsubstituted benzyloxycarbonyl group.

In the general formula (3), n is an integer of 0 to 3 and preferably 2.

Specific compounds represented by the general formula (3) according to the present invention includes:
(S)-3-benzyloxycarbonylamino-2-piperidone,
(R)-3-benzyloxycarbonylamino-2-piperidone,
(S)-3-tert-butyloxycarbonylamino-2-piperidone,
(R)-3-tert-butyloxycarbonylamino-2-piperidone,
(S)-3-benzoylamino-2-piperidone,
(R)-3-benzoylamino-2-piperidone,
(S)-3-acetylamino-2-piperidone,
(R)-3-acetylamino-2-piperidone,
(S)-3-benzyloxycarbonylamino-2-pyrrolidone,
(R)-3-benzyloxycarbonylamino-2-pyrrolidone,
(S)-3-benzyloxycarbonylamino-2-azetidinone,
(R)-3-benzyloxycarbonylamino-2-azetidinone,
(S)-3-benzyloxycarbonylamino-2-perhydroazepinone, and
(R)-3-benzyloxycarbonylamino-2-perhydroazepinone.

Reactions in the preparation method of the present invention is described below.

The silylating agent for reacting with a compound of the general formula (3) includes, for instance, compounds represented by the general formula (6). In the general formula (6), lower alkyl groups represented by R1, R2 and R3 are as described above. Aryl groups represented by R1, R2 and R3 are as described above. All of R1, R2 and R3 are each preferably a methyl group. Halogen atoms represented by X in the general formula (6) include a chlorine atom, a bromine atom or an iodine atom. Fluorinated alkylsulfonates represented by X include trifluoromethanesulfonate and pentafluoroethanesulfonate. X is preferably a chlorine atom.

The sililating agents may be used in an amount within a range of about 0.5 to 20 equivalent and preferably about 1 to 5 equivalent, for a compound of the general formula (3). In the reaction of the compound with the silylating agent, it is considered that hydrogen of a lactam of the general formula (3) is substituted by the silyl group.

The specific sililating agents represented by the general formula (6) according to the present invention include:
trimethylsilyl chloride,
trimethylsilyl bromide,
trimethylsilyl iodide,
trimethylsilyl trifluoromethanesulfonate,
trimethylsilyl pentafluoroethanesulfonate,
dimethylethylsilyl chloride and
dimethylisopropylsilyl chloride.

A solvent for the reaction may be any solvent for making the reaction proceed, and includes, but is not particularly limited to, aromatic hydrocarbons such as benzene, toluene and xylene; ethers such as tetrahydrofuran, dioxane, isopropylether, 2-methoxyethylether and diethylether; hydrocarbons such as hexane, heptane and octane; halogenated hydrocarbons such as chloroform, dichloromethane and 1,2-dichloroethane; esters such as methyl acetate, ethyl acetate and butyl acetate; nitrites such as acetonitrile and propionitrile; and mixed solvents consisting of an appropriate combination of these organic solvents. The solvent is preferably an aromatic hydrocarbon such as toluene or a halogenated hydrocarbon such as dichloromethane, and more preferably toluene. The reaction temperature is in a range of $-50°$ C. to a temperature at which the used solvent is refluxed, and is preferably $-5°$ C. to $60°$ C. The reaction time is not particularly limited to, but is any of time in which the reaction is finished, and is preferably in a range of one minute to 72 hours.

A base may be used in the above reaction as needed. For instance, an organic base such as triethylamine and diisopropylethylamine and an inorganic base such as sodium bicarbonate can be used, but preferably an organic base such as triethylamine and diisopropylethylamine is used. The bases may be used in an amount within a range of 0.5 to 20 equivalent and preferably of 1 to 5 equivalent, for a compound represented by the general formula (3).

The reagent which is used for introducing a phosphoric acid derivative into a lactam ring includes phosphorus oxyhalide represented by $P(=O)T_3$ of the general formula (4). T in $P(=O)T_3$ represents a halogen atom such as a fluorine atom, a chlorine atom and a bromine atom, and preferably is a chlorine atom. Specific examples of $P(=O)T_3$ represented by the general formula (4) include:
phosphorus oxychloride and
phosphorus oxybromide.

Direct addition of the reagent into a reaction solution having finished the silylization, forms a bond between a nitrogen atom on the ring of the compound (3) and a phosphorus atom. The ratio of $P(=O)T_3$ to the compound of the general formula (3) may be in a range of 1 to 20 equivalent, and preferably 3 to 5 equivalent. The reaction time is not limited to, but and may be any time in which the reaction is finished, and preferably is in a range of 12 to 120 hours. The reaction temperature is in a range of $-50°$ C. to the temperature at which a using solvent is refluxed.

Subsequent addition of ammonia to the reaction solution can lead to preparation of a compound of the general formula (5), which is a phosphoric amide. Methods for adding ammonia includes a method for directly feeding a gaseous ammonia to a reaction vessel, a method for adding a liquid ammonia, an ammonia-containing solution such as an aqueous solution, a methanol solution and an ethanol solution of ammonia. A preferable adding method is adding the reaction solution dropwise to an aqueous solution of ammonia. The formed compound (5) can be purified by a normal purification means such as extraction, chromatography, crystallization and suspension purification. The reaction temperature is about $-50°$ C to $60°$ C.

The process for obtaining a compound of the general formula (5) in the preparation method of the present invention, by reacting the compound of the general formula (3) sequentially with a sililating agent, a phosphoric acid derivative and ammonia, can make each compound react in the same solvent without separating it, and make it react in a temperature kept to about −20° C. to 80° C. in all steps.

The specific examples of compounds represented by the general formula (5) according to the present invention include:

(S)-3-benzyloxycarbonylamino-1-diaminophosphinyl-2-piperidone,
(R)-3-benzyloxycarbonylamino-1-diaminophosphinyl-2-piperidone,
(S)-3-tert-butyloxycarbonylamino-1-diaminophosphinyl-2-piperidone,
(R)-3-tert-butyloxycarbonylamino-1-diaminophosphinyl-2-piperidone,
(S)-3-benzoylamino-1-diaminophosphinyl-2-piperidone,
(R)-3-benzoylamino-1-diaminophosphinyl-2-piperidone,
(S)-3-acetylamino-1-diaminophosphinyl-2-piperidone,
(R)-3-acetylamino-1-diaminophosphinyl-2-piperidone,
(S)-3-benzyloxycarbonylamino-1-diaminophosphinyl-2-pyrrolidone,
(R)-3-benzyloxycarbonylamino-1-diaminophosphinyl-2-pyrrolidone,
(S)-3-benzyloxycarbonylamino-1-diaminophosphinyl-2-azetidinone,
(R)-3-benzyloxycarbonylamino-1-diaminophosphinyl-2-azetidinone,
(S)-3-benzyloxycarbonylamino-1-diaminophosphinyl-2-perhydroazepinone and
(R)-3-benzyloxycarbonylamino-1-diamino phosphinyl-2-perhydroazepinone.

A compound of the general formula (7) used in the present invention can be prepared according to JP-A-2000-327689, or can be prepared from the compound (5), described below, by the method according to the present specification.

A protecting group Y, in a compound represented by the above general formula (7) is the same as the protecting group Y of a compound represented by the general formula (1).

In the general formula (7), n is an integer of 0 to 3 and is preferably 2.

Specific examples of compounds represented by the general formula (7) according to the present invention are shown in Table 1.

TABLE 1

| Compound No. | n | Y | C* |
|---|---|---|---|
| 1 | 0 | benzyloxycarbonyl | S |
| 2 | 0 | benzyloxycarbonyl | R |
| 3 | 0 | p-nitrobenzyloxycarbonyl | S |
| 4 | 0 | p-nitrobenzyloxycarbonyl | R |
| 5 | 0 | p-methoxybenzyloxycarbonyl | S |
| 6 | 0 | p-methoxybenzyloxycarbonyl | R |
| 7 | 0 | 3,4-dimethoxy-6-nitrobenzyloxycarbonyl | S |
| 8 | 0 | 3,4-dimethoxy-6-nitrobenzyloxycarbonyl | R |
| 9 | 0 | 2,4-dichlorobenzyloxycarbonyl | S |
| 10 | 0 | 2,4-dichlorobenzyloxycarbonyl | R |
| 11 | 0 | p-bromobenzyloxycarbonyl | S |
| 12 | 0 | p-bromobenzyloxycarbonyl | R |
| 13 | 0 | p-chlorobenzyloxycarbonyl | S |
| 14 | 0 | p-chlorobenzyloxycarbonyl | R |
| 15 | 0 | 9-anthrylmethyloxycarbonyl | S |
| 16 | 0 | 9-anthrylmethyloxycarbonyl | R |
| 17 | 0 | tert-butoxycarbonyl | S |
| 18 | 0 | tert-butoxycarbonyl | R |
| 19 | 1 | benzyloxycarbonyl | S |
| 20 | 1 | benzyloxycarbonyl | R |
| 21 | 1 | p-nitrobenzyloxycarbonyl | S |
| 22 | 1 | p-nitrobenzyloxycarbonyl | R |
| 23 | 1 | p-methoxybenzyloxycarbonyl | S |
| 24 | 1 | p-methoxybenzyloxycarbonyl | R |
| 25 | 1 | 3,4-dimethoxy-6-nitrobenzyloxycarbonyl | S |
| 26 | 1 | 3,4-dimethoxy-6-nitrobenzyloxycarbonyl | R |
| 27 | 1 | 2,4-dichlorobenzyloxycarbonyl | S |
| 28 | 1 | 2,4-dichlorobenzyloxycarbonyl | R |
| 29 | 1 | p-bromobenzyloxycarbonyl | S |
| 30 | 1 | p-bromobenzyloxycarbonyl | R |
| 31 | 1 | p-chlorobenzyloxycarbonyl | S |
| 32 | 1 | p-chlorobenzyloxycarbonyl | R |
| 33 | 1 | 9-anthrylmethyloxycarbonyl | S |
| 34 | 1 | 9-anthrylmethyloxycarbonyl | R |
| 35 | 1 | tert-butoxycarbonyl | S |
| 36 | 1 | tert-butoxycarbonyl | R |
| 37 | 2 | benzyloxycarbonyl | S |
| 38 | 2 | benzyloxycarbonyl | R |
| 39 | 2 | p-nitrobenzyloxycarbonyl | S |
| 40 | 2 | p-nitrobenzyloxycarbonyl | R |
| 41 | 2 | p-methoxybenzyloxycarbonyl | S |
| 42 | 2 | p-methoxybenzyloxycarbonyl | R |
| 43 | 2 | 3,4-dimethoxy-6-nitrobenzyloxycarbonyl | S |
| 44 | 2 | 3,4-dimethoxy-6-nitrobenzyloxycarbonyl | R |
| 45 | 2 | 2,4-dichlorobenzyloxycarbonyl | S |
| 46 | 2 | 2,4-dichlorobenzyloxycarbonyl | R |
| 47 | 2 | p-bromobenzyloxycarbonyl | S |
| 48 | 2 | p-bromobenzyloxycarbonyl | R |
| 49 | 2 | p-chlorobenzyloxycarbonyl | S |
| 50 | 2 | p-chlorobenzyloxycarbonyl | R |
| 51 | 2 | 9-anthrylmethyloxycarbonyl | S |
| 52 | 2 | 9-anthrylmethyloxycarbonyl | R |
| 53 | 2 | tert-butoxycarbonyl | S |
| 54 | 2 | tert-butoxycarbonyl | R |
| 55 | 3 | benzyloxycarbonyl | S |
| 56 | 3 | benzyloxycarbonyl | R |
| 57 | 3 | p-nitrobenzyloxycarbonyl | S |
| 58 | 3 | p-nitrobenzyloxycarbonyl | R |
| 59 | 3 | p-methoxybenzyloxycarbonyl | S |
| 60 | 3 | p-methoxybenzyloxycarbonyl | R |
| 61 | 3 | 3,4-dimethoxy-6-nitrobenzyloxycarbonyl | S |
| 62 | 3 | 3,4-dimethoxy-6-nitrobenzyloxycarbonyl | R |
| 63 | 3 | 2,4-dichlorobenzyloxycarbonyl | S |
| 64 | 3 | 2,4-dichlorobenzyloxycarbonyl | R |
| 65 | 3 | p-bromobenzyloxycarbonyl | S |
| 66 | 3 | p-bromobenzyloxycarbonyl | R |
| 67 | 3 | p-chlorobenzyloxycarbonyl | S |
| 68 | 3 | p-chlorobenzyloxycarbonyl | R |
| 69 | 3 | 9-anthrylmethyloxy carbonyl | S |
| 70 | 3 | 9-anthrylmethyloxycarbonyl | R |
| 71 | 3 | tert-butoxycarbonyl | S |
| 72 | 3 | tert-butoxycarbonyl | R |

A method for preparing an optically active intermediate of sulphostin or analogues thereof of the present invention, is characterized by reacting a compound represented by the general formula (7), where n is an integer of 0 to 3, Y represents a protecting group for the amino group, and a configuration at C* indicates either of S or R, with an optically active amine; and resolving a formed diastereomeric salt with a fractional crystallization, to obtain an optically active amine salt of an optically active compound represented by the general formula (8), where n and Y are as described above; and each configuration at C* and P* may be the same or different and indicates S or R.

The optically active amine in the present invention may be usually any one commercially available which can form a crystalline salt with a diastereomer isomer of the general formula (7), but is preferably a monoacid base, which includes, for instance, derivatives of (+)- or (−)-2-amino-1-phenylethanol represented by the general formula (9), where Ar represents a phenyl group which may have a substituent group; R1' represents a lower alkyl group which may have a substituent group or an aryl group which may have a substituent group; each of R2' and R3' may be the same or different and represents a hydrogen atom or a lower alkyl group; and each configuration at C*1 and C*2 may be the same or different and represents S or R. Each functional group and substituent group in the general formula (9) are as described above.

Optically active amines specifically include, for instance, (1R,2S)-(−)-2-amino-1,2-diphenylethanol, (1S,2R)-(+)-2-amino-1,2-diphenylethanol, (1R,2S)-(−)-ephedrine, (1S,2R)-(+)-ephedrine, (1R,2S)-(−)-N-methylephedrine, (1S,2R)-(+)-N-methylephedrine, (1R,2S)-(−)-4-hydroxyephedrine, (1S,2R)-(+)-4-hydroxyephedrine, (1R,2S)-(−)-norephedrine, (1S,2R)-(+)-norephedrine, (1R,2S)-(−)-3,4-dihydroxynorephedrine, (1S,2R)-(+)-3,4-dihydroxynorephedrine, (1S,2R)-(−)-2-dibutylamino-1-phenyl-1-propanol, (1R,2S)-(+)2-dibutylamino-1-phenyl-1-propanol, (1S,2S)-(+)-pseudoephedrine, (1R,2R)-(−)-pseudoephedrine, (1S,2S)-(+)-N-methylpseudoephedrine, (1R,2R)-(−)-N-methylpseudoephedrine, (1S,2S)-(+)-2-amino-3-methoxy-1-phenyl-1-propanol, (1R,2R)-(−)-2-amino-3-methoxy-1-phenyl-1-propanol, erythro-1,2-diphenyl-2-(propylamino) ethanol, erythro-2-(isopropylamino)-1,2-diphenylethanol, (1R,2R)-(−)-2-amino-1-phenyl-1,3-propanediol, (1S,2S)-(+)-2-amino-1-phenyl-1,3-propanediol, (1R,2R)-(−)-2-amino-1-(4-nitrophenyl)-1,3-propanediol and (1S,2S)-(+)-2-amino-1-(4-nitrophenyl)-1,3-propanediol. Among them, preferable ones are (1R,2S)-(−)-2-amino-1,2-diphenylethanol, (1S,2R)-(+)-2-amino-1,2-diphenylethanol, (1R,2S)-(−)-ephedrine, (1S,2R)-(+)-ephedrine, (1R,2S)-(−)-N-methylephedrine, (1S,2R)-(+)-N-methylephedrine, (1R,2S)-(−)-4-hydroxyephedrine, (1S,2R)-(+)-4-hydroxyephedrine, (1R,2S)-(−)-norephedrine, (1S,2R)-(+)-norephedrine, (1R,2S)-(−)-3,4-dihydroxynorephedrine, (1S,2R)-(+)-3,4-dihydroxynorephedrine, (1S,2R)-(−)-2-dibutylamino-1-phenyl-1-propanol and (1R,2S)-(+)-2-dibutylamino-1-phenyl-1-propanol. Particularly preferable ones are (1S,2R)-(+)-2-amino-1,2-diphenylethanol and (1R,2S)-(−)-2-amino-1,2-diphenylethanol.

When resolving diastereomeric salts by fractional crystallization, compounds to be resolved are usually reacted with an optically active resolving agent to form diastereomeric salts, and only one optically active substance is obtained by utilizing a difference in solubility of the crystal between two types of formed diastereomeric salts. When optically resolving compounds which are enantiomers to one another by fractional crystallization, a resolving agent having a reverse configuration is used.

However, when resolving compounds which are diastereomers to one another represented by the general formula (7) used in the present invention by fractional crystallization, in contrast to optically resolving the above enantiomer compounds, even if using the resolving agent having the reverse configuration, the other diastereomer is not always resolved. Surprisingly, however, the present inventors found that both optically active substances could be obtained by changing the molar ratio of the optically active amine which is used as the resolving agent. This is hereafter described in detail.

As for the molar ratio of the compound of the general formula (7) to the optically active amine which is used as the resolving agent, 0.2-1.4 mol equivalent or 1.5 to 10.0 mol equivalent of the optically active amine based on 1 mol of the compound of the general formula (7) is preferable from a view point of a resolution efficiency, and 0.5-1.2 mol equivalent or 1.8-5.0 mol equivalent is particularly preferable. Depending on the former molar ratio or the latter molar ratio, isomers having different configurations from each other at the phosphorus atom of the compound represented by the general formula (7) can be obtained.

For instance, the reaction of a compound of the general formula (7) where a protecting group Y is a benzyloxycarbonyl group, n is 2 and the configuration is S at C*, with (1S,2R)-(+)-2-amino-1,2-diphenylethanol as an optionally active amine, at the former molar ratio, forms a hardly soluble salt of a compound of the general formula (8) where a protecting group Y is a benzyloxycarbonyl group, n is 2 and the configuration is S at C* and the configuration is S at P*, and (1R,2S)-(−)-2-amino-1,2-diphenylethanol, at a ratio of 1 to 1. Thus, an isomeric amine salt can be obtained at a high yield.

Use of the optically active amine is used at the latter molar ratio, forms a hardly insoluble salt of a compound of the general formula (8) where a protecting group Y is a benzyloxycarbonyl group, n is 2, and the configuration is S at C* and R at P*, and (1S,2R)-(+)-2-amino-1,2-diphenylethanol, at a ratio of 1 to 2. Thus, an isomeric amine salt of which the configuration on the phosphorus atom is reverse to the above one can be obtained at a high yield. This isomer has the same absolute configuration as sulphostin, and is the intermediate which can lead to sulphostin.

When reacting (1R,2S)-(−)-2-amino-1,2-diphenylethanol which is an enantiomer reverse to the above optically active amine with a compound of the general formula (7) where a protecting group Y is a benzyloxycarbonyl group, n is 2, and the configuration is S at C*, the reaction provides a crystalline salt regardless of the added equivalent of the amine, but the salt has little difference in solubility between stereoisomers and the optical resolution cannot be performed.

The reason why the reaction of a compound of the general formula (7) where a protecting group Y is a benzyloxycarbonyl group, n is 2 and the configuration is S at C*, with (1S,2R)-(+)-2-amino-1,2-diphenylethanol of an optically active amine forms a salt at both ratios of 1 to 1 and 1 to 2, and the solubility of the formed salt is reversed, is presumed as follows: Because the compound of the general formula (7) has a sulfonic acid, it forms a salt with one molecule of the optically active amine. When it forms a vis-a-vis (1:1) salt, sulfonic acid is stabilized by the optically active amine; the acidity of the compound of the general formula (7) increases; and the sulfonic acid forms a salt with one more mol equivalent of the optically active amine. It is considered that the salt of 2 mol equivalent causes a phenomenon of reversing the solubility by a change of a crystal structure due to the bimolecular salt. Because the site in the structure of the general formula (7) where the salt is formed with the amine is specified, the above phenomenon is considered to be applicable to a salt formed of a compound where the configuration is S at C* of the general formula (7), with the optically active amine (particularly the optically active amine of the general formula (9)) where the configuration is S at C*1 and R at C*2.

On the other hand, as for a compound having the configuration of R at C* in the general formula (7), when reacting 1 mol of a compound of the general formula (7) with such an optically active amine of the general formula (1) where the configuration is R at C*1 and S at C*2, in an amount of, for instance, 0.2 to 1.4 mol equivalent or 1.5 to 10.0 mol equivalent, preferably 0.5 to 1.2 mol equivalent or 1.8 to 5.0 mol equivalent, the reaction at the former mole ratio forms a hardly soluble salt of a compound of the general formula (8) where the configuration is R at C* and R at P*, and the optically active amine at a ratio of 1 to 1, and the reaction at the latter mole ratio forms a hardly soluble salt of a compound of the general formula (8) where the configuration is R at C* and S at P*, and the optically active amine, at a ratio of 1 to 2.

Specifically, the reaction of a compound of the general formula (7) where a protecting group Y is a benzyloxycarbonyl group, n is 2 and the configuration is R at C*, with (1S,2R)-(−)-2-amino-1,2-diphenylethanol as a resolving agent, at the former mole ratio, forms a hardly soluble salt of a compound of the general formula (8) where a protecting group Y is the benzyloxycarbonyl group, n is 2 and the configuration is R at C* and R at P*, and (1R,2S)-(−)-2-amino-1,2-diphenylethanol, at a ratio of 1 to 1; and the reaction at the latter molar ratio forms a hardly soluble salt of the compound of the general formula (8) where a protecting group Y is a benzyloxycarbonyl group, n is 2 and a configuration is R at C* and S at P*, and (1R,2S)-(−)-2-amino-1,2-diphenylethanol, at a ratio of 1 to 2. Thus, each isomeric amine salt can be obtained at a high yield.

Solvents usually used for fractional crystallization include water; alcohols such as methanol, ethanol, 1-propanol, 2-propanol, 1-butanol and 2-butanol; ketones such as acetone, methylethylketone, methylisobutylketone, diethylketone, di-n-propylketone, diisopropylketone and methylisopropylketone; aromatic hydrocarbons such as benzene, toluene and xylene; ethers such as tetrahydrofuran, dioxane, isopropylether, 2-methoxyethylether and diethylether; hydrocarbons such as hexane, heptane and octane; halogenated hydrocarbons such as chloroform, dichloromethane and 1,2-dichloroethane; esters such as methyl acetate, ethyl acetate and butyl acetate; nitryls such as acetonitril and propionitril; and a mixed solvent of suitable combination of these solvents: and preferably include water, alcohols such as methanol, ethanol, 1-propanol and 2-propanol, and a mixed solvent. The quantity to be used varies depending on the kinds of a solvent to be used, a compound of a general formula (7) and an optically active amine. The rough standard is the quantity of the solvent in which most of a salt of a diastereomer with lower solubility is crystallied. The quantity of the solvent to be used for the fractional crystallization is roughly about 1 to 1,000 mL for 1 g of a diastereomeric salt, and is preferably about 2 to 200 mL.

The crystallization may be carried out by stirring the solution at a temperature of −50° C. to a boiling point of a solvent to be used, preferably at a temperature of −10° C. to −110° C., and for 1 minute to 120 hours, to accumulate a diastereomeric salt having a lower solubility in the solvent out of the two kinds of diastereomeric salts, then cooling the solution to a temperature of −30° C. to 40° C., and separating a precipitated diastereomeric salt.

Thus obtained diastereomeric salt, after a protecting group Y for an amino group and an optically active amine are removed therefrom, can be led to sulphostin or analogues thereof represented by the general formula (1). This preparation method is also included by the present invention. As for removing the protecting group, a method suitable for each protecting group may be employed, and a well-known method is employed. For instance, a benzyloxycarbonyl group can be removed by hydrogenation decomposition through catalytic reduction, a tert-butoxycarbonyl group by acid treatment, a p-methoxybenzyloxycarbonyl group by hydrogenation decomposition through catalytic reduction or by acid treatment.

The compound represented by the general formula (1) produced by the above method, has the same behaviour in chromatography, physico-chemical properties, an inhibitory effect against dipeptidyl peptidase IV as those of sulphostin and sulphostin analogues according to JP-A-2000-327689.

In addition, the steps of; dissolving a compound represented by the general formula (5') (wherein n denotes an integer of 0 to 3; Y represents a protecting group for an amino group; and a configuration at C* and P* may be each the same or different and indicates S or R) provided by the method of JP-A-2000-327689, in a solvent such as DMF; sulfonating it with sulfur trioxide, specifically sulfur trioxide, a sulfur trioxide-pyridine complex, a sulfur trioxide-trimethyl amine complex or a sulfur trioxide-N,N-dimethylformamide complex; then without isolating the formed compound of the general formula (7), resolving it by fractional crystallization using the optically active amine described above; and further deprotecting the amino group, can provide optically active sulphostin or the analogues thereof. This preparation method is also included by the present invention.

Furthermore, by combining the preparation steps described above, the sulphostin and the sulphostin analogues represented by the general formula (4) can be prepared from the compound of the general formula (1). Such a serial preparation method is also included by the present patent.

The present invention includes a salt of an optically active compound represented by the general formula (8) (wherein n denotes an integer of 0 to 3; Y represents a protecting group for an amino group; and a configuration at C* and P* may be each the same or different and indicates S or R ) and an optically active amine represented by the general formula (9) (wherein Ar denotes a phenyl group which may have a substituent group; R1' indicates a lower alkyl group which may have a substituent group or an aryl which may have a substituent group; R2' and R3' may be each the same or different and indicates a hydrogen atom or a lower alkyl group; and a configuration at C*1 and C*2 may be each the same or different and indicates S or R). The protecting group Y for the amino group in the general formula (8) includes the same groups as the protecting group Y for the amino group in the above general formula (7). The preferred groups are also described above. The n in the general formula (8) is the same as in the general formula (7), and is preferably 2. The optically active amine which is represented by the general formula (9) includes the amine compound described in the above preparation method, and the preferred compound is also described above. Naturally, an monoamine salt and a diamine salt are also included in the present invention.

The amines specifically include, for instance, (1S,2R)-(+)-2-amino-1,2-diphenylethanol salts of (3S)-3-benzyloxycarbonylamino-(S)-1-amino(sulfoamino)phosphinyl-2-piperidone, (3S)-3-p-nitrobenzyloxycarbonylamino-(S)-1-amino (sulfoamino)phosphinyl-2-piperidone, (3S)-3-p-methoxybenzyloxycarbonylamino-(S)-1-amino (sulfoamino)phosphinyl-2-piperidone, (3S)-3-(3,4-dimethoxy-6-nitrobenzyloxycarbonyl)amino-(S)-1-amino (sulfoamino)phosphinyl-2-piperidone, (3S)-3-(2,4-dichlorobenzyloxycarbonyl)amino-(S)-1-amino (sulfoamino)phosphinyl-2-piperidone, (3S)-3-p-bromobenzyloxycarbonylamino-(S)-1-amino(sulfoamino)phosphinyl-2-piperidone, (3S)-3-p-chlorobenzyloxycarbonylamino-(S)-1-amino(sulfoamino)phosphinyl-2-piperidone, (3S)-3-(9-anthrylmethyloxycarbonyl)amino-(S)-1-amino(sulfoamino) phosphinyl-2-piperidone and (3S)-3-tert-butoxycarbonylamino-(S)-1-amino(sulfoamino)phosphinyl-2-piperidone; 2{(1S,2R)-(+)-2-amino-1,2-diphenylethanol} salts of (3S)-3-benzyloxycarbonylamino-(R)-1-amino(sulfoamino)phosphinyl-2-piperidone, (3S)-3-p-nitrobenzyloxycarbonylamino-(R)-1-amino(sulfoamino)phosphinyl-2-piperidone, (3S)-3-p-methoxybenzyloxycarbonylamino-(R)-1-amino(sulfoamino)phosphinyl-2-piperidone, (3S)-3-(3,4-dimethoxy-6-nitrobenzyloxycarbonyl)amino-(R)-1- amino(sulfoamino)phosphinyl-2-piperidone, (3S)-3-(2,4-dichloro benzyloxycarbonyl)amino-(R)-1-amino (sulfoamino)phosphinyl-2-piperidone, (3S)-3-parabromobenzyloxycarbonylamino-(R)-1-amino (sulfoamino)phosphinyl-2-piperidone, (3S)-3-p-chlorobenzyloxycarbonylamino-(R)-1-amino(sulfoamino) phosphinyl-2-piperidone, (3S)-3-(9-anthrylmethyloxycarbonyl)amino-(R)-1-amino(sulfoamino) phosphinyl-2-piperidone and (3S)-3-tert-butoxycarbonylamino-(R)-1-amino(sulfoamino)phosphinyl-2-piperidone; (1R,2S)-(−)-2-amino-1,2-diphenylethanol salts of (3R)-3-benzyloxycarbonylamino-(R)-1-amino(sulfoamino)phosphinyl-2-piperidone, (3R)-3-p-nitrobenzyloxycarbonylamino-(R)-1-amino(sulfoamino)phosphinyl-2-piperidone, (3R)-3-p-methoxybenzyloxycarbonylamino-(R)-1-amino(sulfoamino)phosphinyl-2-piperidone, (3R)-3-(3,4-dimethoxy-6-nitrobenzyloxycarbonyl)amino-(R)-1-amino(sulfoamino)phosphinyl-2-piperidone, (3R)-3-(2,4-dichlorobenzyloxycarbonyl)amino-(R)-1-amino (sulfoamino)phosphinyl-2-piperidone, (3R)-3-p-bromobenzyloxycarbonylamino-(R)-1-amino(sulfoamino) phosphinyl-2-piperidone, (3R)-3-p-chlorobenzyloxycarbonylamino-(R)-1-amino(sulfoamino) phosphinyl-2-piperidone, (3R)-3-(9-anthrylmethyloxycarbonyl)amino-(R)-1-amino(sulfoamino) phosphinyl-2-piperidone and (3R)-3-tert-butoxycarbonylamino-(R)-1-amino(sulfoamino)phosphinyl-2-piperidone; and 2{(1R, 2S)-(−)-2-amino-1,2-diphenylethanol} salts of (3R)-3-benzyloxycarbonylamino-(S)-1-amino(sulfoamino)phosphinyl-2-piperidone, (3R)-3-p-nitrobenzyloxycarbonylamino-(S)-1-amino(sulfoamino) phosphinyl-2-piperidone, (3R)-3-p-methoxybenzyloxycarbonylamino-(S)-1-amino (sulfoamino)phosphinyl-2-piperidone, (3R)-3-(3,4-dimethoxy-6-nitrobenzyloxycarbonyl)amino-(S)-1-amino (sulfoamino)phosphinyl-2-piperidone, (3R)-3-(2,4-dichlorobenzyloxycarbonyl)amino-(S)-1-amino (sulfoamino)phosphinyl-2-piperidone, (3R)-3-p-bromobenzyloxycarbonylamino-(S)-1-amino(sulfoamino) phosphinyl-2-piperidone, (3R)-3-p-chlorobenzyloxycarbonylamino-(S)-1-amino(sulfoamino) phosphinyl-2-piperidone, (3R)-3-(9-anthrylmethyloxycarbonyl)amino-(S)-1-amino(sulfoamino) phosphinyl-2-piperidone and (3R)-3-tert-butoxycarbonylamino-(S)-1-amino(sulfoamino)phosphinyl-2-piperidone.

The present invention is specifically explained below with reference to the following examples, but is not limited to them. Room temperature hereafter means 10° C. to 30° C. NMR value in the examples is δ (ppm) measured by using tetramethylsilane (TMS) or sodium salt of 3-(trimethylsilyl) propionic-2,2,3,3-$d_4$-acid (TSP) as an internal standard.

The optical purity (d.e.) of a phosphorus atom was measured in the following method.

20 mg (1.0 eq.) of a resulting compound and 33 mg (5.0 eq.) of sodium bicarbonate were dissolved into 10 mL of water, and 5 mL of tetrahydrofuran (THF) was added thereto. Then, 25 μL (2.5 eq.) of benzyloxycarbonyl chloride was added thereto, the solution was stirred for 30 minutes so that the amino group was benzyloxycarbonylated. The reaction mixture was analyzed with a high-speed liquid chromatography using an ODS column (PEGASIL ODS made by SSC Sensyu science Co., Ltd.).

EXAMPLE 1

(S)-3-benzyloxycarbonylamino-1-diaminophosphinyl-2-piperidone 600 g (2.42 mol) of (S)-3-benzyloxycarbonylamino-2-piperidone was added to 6 L of toluene and 823 mL (4.80 mol) of diisopropylethylamine, subsequently 612 mL (4.80 mol) of trimethylsilyl chloride was added dropwise, and the solution was stirred at room temperature for 24 hours. Subsequently, 894 mL (9.60 mol) of phosphorus oxychloride was added dropwise, and the solution was stirred at room temperature for 48 hours. An ammonia water adjusted to a pH of about 10 with ammonium chloride was cooled to −10° C. or lower, and the reacted solution was added dropwise into it. When the pH falls to less than 9, the ammonia water was added. The obtained suspension was filtered, and the residue was washed with 3 L of toluene, subsequently 2 L of a toluene-THF mixed solvent, and then extracted with 10 L of a THF-methanol mixed solvent. The extracted liquid was vacuum-concentrated, the residue was washed with 6 L of water and suspension-purified with 10 L of an ethanol-diisopropylether mixed solvent, and 345.7 g of (S)-3-benzyloxycarbonylamino-1-diamino phosphinyl-2-piperidone (1.06 mol and a yield of 43.8%) was obtained.

$^1$H-NMR (200 MHzFT, TMS, DMSO-D6) 1.58-1.66 (1H, m), 1.73-1.78 (2H, m), 1.98-2.03 (1H, m), 3.43-3.48 (1H, m), 3.55-3.61 (1H, m), 4.06-4.12 (1H, m), 4.14 (2H, brs), 4.19 (2H, brs), 5.00 (2H, s), 7.28-7.41 (6H, m).

The compound was analyzed with high-speed liquid chromatography by using an optically active column (CHIRALPACK AS made by Daicel Chemical Industries, Ltd.) to prove to have an optical purity (ee) of higher than 99%.

EXAMPLE 2

Preparation of a Salt of (3S)-3-benzyloxycarbonylamino-(S)-1-amino(sulfoamino)phosphinyl-2-piperidone with (1S,2R)-(+)-2-amino-1,2-diphenylethanol 50 mL of water and 2.45 mL of 1 N hydrochloric acid was added to 1.05 g (2.35 mmol) of a mixture of a sodium salt of (3S)-3-benzyloxycarbonylamino-(S)-1-amino (sulfoamino) phosphinyl-2-piperidone and a sodium salt of (3S)-3-benzyloxycarbonylamino-(R)-1-amino (sulfoamino) phosphinyl-2-piperidone at about 1:1, which are obtained according to JP-A-2000-327689, and 522 mg (2.45 mmol) of (1S, 2R)-(+)-2-amino-1, 2-diphenylethanol; and the reaction liquid was stirred while being heated. Both compounds were completely dissolved at an inner temperature of about 50° C., heating was stopped, and the reaction liquid was left till the inner temperature becomes room temperature. The precipitated crystal was taken through filtration, and 656 mg of a salt of (3S)-3-benzyloxycarbonylamino-(S)-1-amino(sulfoamino)phosphinyl-2-piperidone with (1S, 2R)-(+)-2-amino-1,2-diphenylethanol (1.06 mmol, an optical purity (d.e.) of 90%, and a yield of 45%) was obtained. As a result of measuring the optical purity (d.e.) of the filtrate, it proved to contain (3S)-3-benzyloxycarbonylamino-(R)-1-amino(sulfoamino)-phosphinyl-2-piperidone of 90% (d.e.).

salt of (3S)-3-benzyloxycarbonylamino-(S)-1-amino (sulfoamino) phosphinyl-2-piperidone with (1S, 2R)-(+)-2-amino-1,2-diphenylethanol ¹H-NMR (200 MHzFT, TMS, CD₃OD) 1.65-2.00 (3H, m), 2.12-2.20 (1H, m), 3.50-3.88 (2H, m), 4.16-4.30 (1H, m), 4.46 (1H, d, J=4.1 Hz), 5.08 (2H, s), 5.22 (1H, d, J=4.1 Hz), 7.04-7.42 (15H, m)

EXAMPLE 3

Preparation of (3S)-3-amino-(S)-1-amino(sulfoamino)phosphinyl-2-piperidone 3.68 g of Palladium black was added to a suspending solution containing 73.56 g (119 mmol) of the salt of (3S)-3-benzyloxycarbonylamino-(S)-1-amino(sulfoamino)phosphinyl-2-piperidone with (1S, 2R)-(+)-2-amino-1,2-diphenylethanol in 150 mL of acetic acid and 375 mL of water, and the solution was stirred in a hydrogen flow at room temperature for 24 hours. The catalyst was removed by filtration (with the use of 500 mL of water for washing) from the reacted solution, and 2.0 L of ethanol was added dropwise to the obtained filtrate. The precipitated crystal was taken through filtration, and 24.5 g of (3S)-3-amino-(S)-1-amino(sulfoamino)phosphinyl-2-piperidone (84.4 mmol, an optical purity (d.e.) of 98.5%, and a yield of 71%) was obtained.

(3S)-3-amino-(S)-1-amino(sulfoamino)phosphinyl-2-piperidone

¹H-NMR (400 MHzFT, TSP, D₂O) 1.85-2.12 (3H, m), 2.37-2.45 (1H, m), 3.63-3.74 (2H, m), 4.13 (1H, dd, J=6.5, 7.0 Hz) ¹³C-NMR (100 MHzFT, TSP, D₂O) 23.1, 26.7, 47.8, 53.4, 174.5 MS (FAB, POS) m/Z: 273 [M+H]⁺ [α] $D^{20}$=+43.8° (water, c=0.5)

EXAMPLE 4

Preparation of the salt of (3S)-3-benzyloxycarbonylamino-(R)-1-amino(sulfoamino)phosphinyl-2-piperidone with 2{(1S,2R)-(+)-2-amino-1,2-diphenylethanol}

350 mL of ethanol, 200 mL of water and 16.2 mL of 1 N hydrochloric acid were added to 6.94 g (16.2 mmol) of a mixture containing a sodium salt of (3S)-3-benzyloxycarbonylamino-(S)-1-amino(sulfoamino)phosphinyl-2-piperidone and a sodium salt of (3S)-3-benzyloxycarbonylamino-(R)-1-amino(sulfoamino)phosphinyl-2-piperidone at about 1:1, and 7.96 g (37.3 mmol) of (1S, 2R)-(+)-2-amino-1,2-diphenylethanol, and the reaction liquid was stirred while being heating. Both compounds were completely dissolved at an inner temperature of about 55° C., heating was stopped, and the reaction liquid was left till the inner temperature becomes room temperature. The precipitated crystal was taken through filtration, and 5.4 g of a salt of (3S)-3-benzyloxycarbonylamino-(R)-1-amino(sulfoamino) phosphinyl-2-piperidone with 2{(1S,2R)-(+)-2-amino-1,2-diphenylethanol} (6.48 mmol, an optical purity (d.e.) of 95%, and a yield of 40%) was obtained. As a result of measuring the optical purity (d.e.) of the filtrate, it proved to contain (3S)-3-benzyloxycarbonylamino-(S)-1-amino(sulfoamino)phosphinyl-2-piperidone of 80% (d.e.).

salt of (3S)-3-benzyloxycarbonylamino-(R)-1-amino(sulfoamino)phosphinyl-2-piperidone with 2{(1S, 2R)-(+)-2-amino-1,2-diphenylethanol}

¹H-NMR (200 MHzFT, TMS, CD₃OD) 1.65-1.90 (2H, m), 1.95-2.25 (2H, m), 3.50-3.68 (1H, m), 3.75-3.94 (1H, m), 4.20-4.34 (3H, m), 5.04 (2H, d, J=4.9 Hz), 5.09 (2H, s), 7.10-7.40 (25H, m)

EXAMPLE 5

Preparation of (3S)-3-amino-(R)-1-amino(sulfoamino)phosphinyl-2-piperidone (sulphostin)

50 mg of palladium black was added to a suspension containing 1.0 g (1.20 mmol) of the salt of (3S)-3-benzyloxycarbonylamino-(R)-1-amino(sulfoamino)phosphinyl-2-piperidone with 2{(1S,2R)-(+)-2-amino-1,2-diphenylethanol} in 2 mL of acetic acid and 5 mL of water, and the solution was stirred in a hydrogen flow at room temperature for 2 hours. The catalyst was removed by filtration (with the use of water of 6 mL for washing) from the reacted solution, and 21 mL of ethanol was added dropwise to the obtained filtrate. The precipitated crystal was taken through filtration, and 281 mg of (3S)-3-amino-(R)-1-amino(sulfoamino)phosphinyl-2-piperidone (0.968 mmol, an optical purity (d.e.) of 98.6%, and a yield of 81%) was obtained. Then, the product was recrystalized with the use of a water-ethanol solvent, and the desired (3S)-3-amino-(R)-1-amino(sulfoamino)phosphinyl-2-piperidone (sulphostin) (a chemical purity of more than 99%, and an optical purity (d.e.) of more than 99%) was obtained.

(3S)-3-amino-(R)-1-amino(sulfoamino)phosphinyl-2-piperidone (sulphostin)

¹H-NMR (400MHzFT, TSP, D₂O) 1.85-2.02 (2H, m), 2.06-2.17 (1H, m), 2.35-2.45 (1H, m), 3.61-3.69 (1H, m), 3.74-3.83 (1H, m), 4.15 (1H, dd, J=6.9,11.9 Hz) ¹³C-NMR (100 MHzFT, TSP, D₂O) 22.6, 26.3, 47.5, 53.4, 174.5 MS (ESI, NEG) m/Z: 271 [M–H]⁻[α] $D^{20}$=–21.8° (water, c=5.03)

EXAMPLE 6

Preparation of the Salt of (3R)-3-benzyloxycarbonylamino-(R)-1-amino (sulfoamino) phosphinyl-2-piperidone with (1R,2S)-(–)-2-amino-1,2-diphenylethanol 5.0 mL of water and 0.21 mL of 1 N hydrochloric acid was added to 90 mg (0.21 mmol) of a mixture of a sodium salt of (3S)-3-benzyloxycarbonylamino-(R)-1-amino(sulfoamino) phosphinyl-2-piperidone and a sodium salt of (3R)-3-benzyloxycarbonylamino-(S)-1-amino(sulfoamino)phosphinyl-2-piperidone at about 1:1, and 42.6 mg (0.20 mmol) of (1R, 2S)-(–)-2-amino-1,2-diphenylethanol; and the reaction liquid was stirred while being heated. Both compounds were completely dissolved at an inner temperature of about 50° C., heating was stopped, and the reaction liquid was left till the inner temperature becomes room temperature. The precipitated crystal was taken through a filter, and 25 mg of a salt of (3R)-3-benzyloxycarbonylamino-(R)-1-amino(sulfoamino) phosphinyl-2-piperidone with (1R,2S)-(–)-2-amino-1,2-diphenylethanol (0.040 mmol, an optical purity (d.e.) of 95%, and a yield of 19%) was obtained.

salt of (3R)-3-benzyloxycarbonylamino-(R)-1-amino(sulfoamino)phosphinyl-2-piperidone with (1R,2S)-(–)-2-amino-1,2-diphenylethanol ¹H-NMR (200 MHzFT, TMS, CD₃OD) 1.63-2.02 (3H, m), 2.12-2.30 (1H, m), 3.50-3.88 (2H, m), 4.17-4.30 (1H, m), 4.46 (1H, d, J=4.0 Hz), 5.08 (2H, s), 5.22 (1H, d, J=4.0 Hz), 7.04-7.41 (15H, m)

EXAMPLE 7

Preparation of (3R)-3-amino-(R)-1-amino(sulfoamino)phosphinyl-2-piperidone 90 mg of Palladium black was added to a suspension containing 1.35 g (2.18 mmol) of the salt of (3S)-3-benzyloxycarbonylamino-(R)-1-amino(sulfoamino)phosphinyl-2-piperidone with (1R, 2S)-(−)-2-amino-1,2-diphenylethanol of in 3 mL of acetic acid and 15 mL of water, and the solution was stirred in a hydrogen flow at room temperature for 24 hours. The catalyst was removed by filtration (with the use of 15 mL of water for washing) from the reacted solution, and 80 mL of ethanol was added dropwise to the obtained filtrate. The precipitated crystal was taken through a filter, and 304 mg of (3R)-3-amino-(R)-1-amino(sulfoamino)phosphinyl-2-piperidone (1.05 mmol, an optical purity (d.e.) of 95.4%, and a yield of 48%) was obtained.

(3R)-3-amino-(R)-1-amino( sulfoamino)phosphinyl-2-piperidone $^1$H-NMR (200 MHzFT, TSP, D$_2$O) 1.79-2.12 (3H, m), 2.33-2.48 (1H, m), 3.65-3.74 (2H, m), 4.15 (1H, dd, J=7.4, 11.4 Hz) MS (FAB, POS) m/Z: 273[M+H]$^+$ [α]$_D^{20}$=−43.6° (water, c=0.5)

EXAMPLE 8

Preparation of the Salt of (3R)-3-benzyloxycarbonylamino-(S)-1-amino(sulfoamino)phosphinyl-2-piperidone with 2{(1R,2S)-(−)-2-amino-1,2-diphenylethanol}

125 mL of ethanol, 95 mL of water and 5.6 mL of 1 N hydrochloric acid were added to 2.4 g (5.60 mmol) of a mixture of the sodium salt of (3R)-3-benzyloxycarbonylamino-(S)-1-amino(sulfoamino)phosphinyl-2-piperidone and the sodium salt of (3R)-3-benzyloxycarbonylamino-(R)-1-amino(sulfoamino)phosphinyl-2-piperidone at about 1:1, and 2.63 mg (12.3 mmol) of (1R,2S)-(−)-2-amino-1,2-diphenylethanol; and the reaction liquid was stirred while being heated. Both compounds were completely dissolved at an inner temperature of about 50° C., heating was stopped, and the reaction liquid was left till the inner temperature becomes room temperature. The precipitated crystal was taken through a filter, and 1.95 g of a salt of (3R)-3-benzyloxycarbonylamino-(S)-1-amino(sulfoamino) phosphinyl-2-piperidone with 2{(1R,2S)-(−)-2-amino-1,2-diphenylethanol} (2.34 mmol, an optical purity (d.e.) of 95.6%, and a yield of 42%) was obtained. As a result of measuring the optical purity (d.e.) of the filtrate, the filtrate proved to contain (3R)-3-benzyloxycarbonylamino-(R)-1-amino(sulfoamino)phosphinyl-2-piperidone of 83.4% (d.e.).

salt of (3R)-3-benzyloxycarbonylamino-(S)-1-amino(sulfoamino)phosphinyl-2-piperidone with 2{(1R,2S)-(−)-2-amino-1,2-diphenylethanol}

$^1$H-NMR (200 MHzFT, TMS, CD$_3$OD) 1.55-1.77 (2H, m), 1.85-2.05 (2H, m), 3.00-3.80 (2H, m), 4.18-4.30 (3H, m), 4.86 (2H, d, J=4.8 Hz), 5.08 (2H, s), 7.07-7.43 (25H, m)

EXAMPLE 9

Preparation of (3R)-3-amino-(S)-1-amino(sulfoamino)phosphinyl-2-piperidone 140 mg of palladium black was added to a suspension containing 2.7 g (3.24 mmol) of the salt of (3R)-3-benzyloxycarbonylamino-(S)-1-amino(sulfoamino)phosphinyl-2-piperidone with 2{(1R,2S)-(−)-2-amino-1,2-diphenylethanol} in 5 mL of acetic acid and 25 mL of water, and the solution was stirred in a hydrogen flow at room temperature for 24 hours. The catalyst was removed by filtration (with the use of 15 mL of water for washing) from the reacted solution, and 80 mL of ethanol was added dropwise to the obtained filtrate. The precipitated crystal was taken through a filter, and 711 mg of (3R)-3-amino-(S)-1-amino(sulfoamino)phosphinyl-2-piperidone (2.45 mmol, an optical purity (d.e.) of 98.8%, and a yield of 76%) was obtained.

(3R)-3-amino-(S)-1-amino(sulfoamino)phosphinyl-2-piperidone $^1$H-NMR (200 MHzFT, TSP, D$_2$O) 1.79-2.24 (3H, m), 2.30-2.47 (1H, m), 3.56-3.90 (2H, m), 4.15 (1H, dd, J=7.3, 11.2 Hz) MS (FAB, POS) m/Z: 273 [M+H]$^+$ [α]$_D^{20}$=+21.5° (water, c=0.5)

EXAMPLE 10

Preparation of (3S)-3-amino-(R)-1-amino(sulfoamino)phosphinyl-2-piperidone (sulphostin)

294 g (0.901 mol) of (S)-3-benzyloxycarbonylamino-1-diaminophosphinyl-2-piperidone described in JP-A-2000-327689 was dissolved in 3.0 L of DMF heated to 60° C., then the reaction liquid was cooled to 10° C. or lower, 172 g (1.08 mol) of the sulfur trioxide-pyridine complex was added to it, and the reaction liquid was stirred for one hour. To the reaction liquid, 100 mL of water, then 1.0 L of methanol and a half of 4.0 L of a solution in methanol containing 480 g (2.25 mol) of (1S, 2R)-(+)-2-amino-1,2-diphenylethanol, which had been prepared beforehand, were added, and the reaction liquid was heated to 50° C. at the inner temperature. The remaining methanol solution of (1S,2R)-(+)-2-amino-1,2-diphenylethanol was all added, the solution was stirred for 30 minutes, then the precipitated crystal was removed through a filter, and methanol in the filtrate was vacuum concentrated. 15.0 L of ethanol and 6.0 L of water were added to the obtained residue, the liquid was stirred for 16 hours, and the precipitated crystal was taken through a filter so that 257 g of the salt of (3S)-3-benzyloxycarbonylamino-(R)-1-amino(sulfoamino)phosphinyl-2-piperidone with 2{(1S,2R)-(+)-2-amino-1,2-diphenylethanol} (an optical purity of 92% d.e.) was obtained.

11 g of palladium black was added to a suspension containing 257 g of the resultant salt of (3S)-3-benzyloxycarbonylamino-(R)-1-amino(sulfoamino)phosphinyl-2-piperidone with 2{(1S,2R)-(+)-2-amino-1,2-diphenylethanol} in 400 mL of acetic acid and 2.0 L of water, and the solution was stirred in a hydrogen flow at room temperature for 3 hours. The catalyst was removed by filtration (with the use of water of 500 mL for washing) from the reacted solution, and 5.0 L of ethanol was added dropwise to the resultant filtrate. The precipitated crystal was taken through a filter, and 59.5 g of (3S)-3-amino-(R)-1-amino(sulfoamino)phosphinyl-2-piperidone (0.205 mol, an optical purity (d.e.) of 97.6%, and a yield from (S)-3-benzyloxycarbonylamino-1-diaminophosphinyl-2-piperidone of 23%) was obtained. Then, the product was recrystalized with the use of a water-ethanol solution, and the desired (3S)-3-amino-(R)-1-amino(sulfoamino)phosphinyl-2-piperidone (sulphostin) (a chemical purity of more than 99%, and an optical purity (d.e.) of more than 99%) was obtained.

INDUSTRIAL APPLICABILITY

The present invention enables the preparation of optically active sulphostin and analogues of sulphostin having dipeptidylpeptidase IV inhibitory activity represented by the general formula (1), and compounds as preparation intermediates thereof represented by the general formula (5) or (8), in an easier way and a larger quantity as compared to the conventional techniques and at a superior purity and yield.

What is claimed is:

1. A method for preparing a compound represented by the following general formula (5)

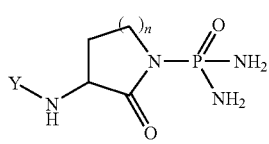

(5)

where, n is an integer of 0 to 3; and Y represents a protecting group for an amino group, comprising the steps of reacting a compound represented by the following general formula (3)

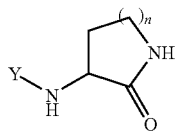

(3)

where, n and Y are as described above, with a sililating agent, represented by the following general formula (6)

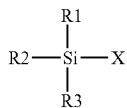

(6)

where R1, R2 and R3 each independently represent a lower alkyl group or an aryl group; and X represents a halogen atom or a fluorinated alkyl sulfonate, subsequently reacting it with a phosphorus oxyhalide represented by the general formula (4)

$$P(=O)T_3 \quad (4)$$

where T represents a halogen atom and further with ammonia, wherein a reaction temperature is −20°C. to 80° in the steps of preparing a compound represented by the general formula (5) from a compound represented by the general formula (3).

2. The preparing method according to claim 1, wherein the Y is a protecting group of a carbamate type or an amide type.

3. The preparation method according to claim 2, wherein the Y is a benzyloxycarbonyl group or a tert-butoxycarbonyl group optionally substituted, and n is 2.

4. The preparation method according to claim 1, wherein the compound represented by the general formula (3) is an optically active substance.

5. The preparation method according to claim 1, wherein T is a chlorine atom in the general formula (4).

6. The preparation method according to claim 1, wherein the silylating agent is trimethylsilyl chloride.

7. A method for preparing an optically active intermediate of optically active sulphostin or an analogue thereof, which is an optically active amine salt of the optically active compound represented by the following general formula (8)

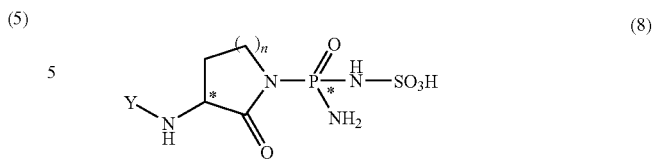

(8)

where n is an integer of 0 to 3; Y represents a protecting group for the amino group; and each configuration at C* and P* may be the same or different and indicates S or R, comprising the steps of resolving the diastereomeric salt formed by reacting a compound represented by the following general formula (7)

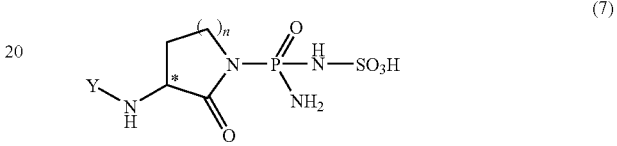

(7)

where n and Y are as described above; and the configuration of C* indicates either of S or R, with an optically active amine, represented by (1R,2S)-(−)-2-diphenylethanol or (1S,2R)-(+)-2-amino-1,2-diphenylethanol, and resolving a formed diastereomeric salt by fractional crystallization.

8. A method for preparing an optically active sulphostin or an analogue thereof represented by the following general formula (1)

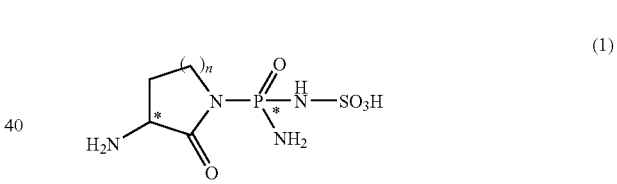

(1)

where n is an integer of 0 to 3; and each configuration of C* and P* may be the same or different and indicates S or R, comprising the steps of reacting a compound represented by the following general formula (7)

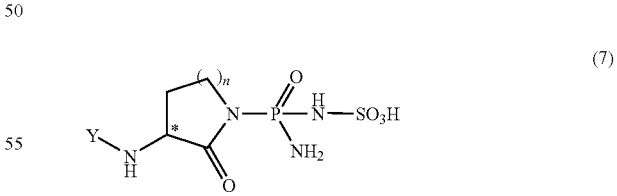

(7)

where n is an integer of 1 to 3, Y represents a protecting group for an amino group; and a configuration of C* indicates either of S or R, with an optically active amine, represented by (1R,2S)-(−)-2-amino-1,2-diphenylethanol or (1S,2R)-(+)-2-diphenylethanol, resolving a formed diastereomeric salt by fractional crystallization to obtain an optically active amine salt of an optically active compound represented by the following general formula (8)

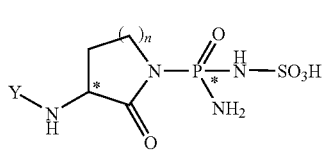

(8)

where n is an integer of 1 to 3, Y represents the protecting group for the amino group; C* and P* have the same meanings as above, and then removing the protecting group for the amino group and the optically active amine by a conventional process.

9. The method according to claim 7 or 8, wherein the Y in the general formula (7) is a protecting group of a carbamate type or an amide type.

10. The method according to claim 7 or 8, wherein the Y in the general formula (7) is a benzyloxycarbonyl group or a tert-butoxycarbonyl group that may have a substituent group; and n is 2.

11. The method according to claim 7 or 8, wherein the Y in the general formula (7) is an unsubstituted benzyloxycarbonyl group; and n is 2.

12. The method according to claim 7 or 8, wherein the compound having the configuration of S at C* and the configuration of S at P* in the general formula (8) is obtained by reacting 1 mol of a compound having the configuration of S at C* in the above general formula (7), with 0.2 to 1.4 mol equivalent of (1S,2R)-(+)-2-amino-1,2-diphenylethanol, as a hardly soluble salt consisting of 1 part of itself and 1 part (1S,2R)-(+)-2-amino-1,2-diphenylethanol.

13. The method according to claim 7 or 8, wherein the compound having the configuration of S at C* and the configuration of R at P* in the general formula (8) is obtained by reacting 1 mol of a compound having the configuration of S at C* in the general formula (7), with 1.5 to 10.0 mol equivalent of (1S,2R)-(+)-2-amino-1,2-diphenylethanol, as a hardly soluble salt consisting of 1 part of itself and 2 parts of (1S,2R)-(+)-2-amino-1,2-diphenylethanol.

14. The method according to any claim 7 or 8, wherein the compound having the configuration of R at C* and the configuration of R at P* in the general formula (8) is obtained by reacting 1 mol of a compound having the configuration of R at C* in the above general formula (7), with 0.2 to 1.4 mol equivalent of(1R,2S)-(−)-2-amino-1,2-diphenylethenol, as a hardly soluble salt consisting of 1 part of itself and 1 part of (1R,2S)-(−)-2-amino-1,2-diphenylethanol.

15. The method according to claim 7 or 8, wherein the compound having the configuration of R at C* and the configuration of S at P* in the general formula (8) is obtained by reacting 1 mol of a compound having the configuration of R at C* in the general formula (7), with 1.5 to 10.0 mol equivalent of (1R,2S)-(−)-2-amino-1,2-diphenylethanol, as a hardly soluble salt consisting of 1 part of itself and 2 parts of (1R,2S)-(−)-2-amino-1,2-diphenylethanol.

16. The method according to claim 7, wherein the optically active amine salt of an optically active substance represented by the following general formula (8)

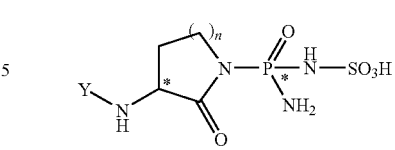

(8)

where n is an integer of 0 to 3; Y represents a protecting group for the amino group; and each configuration at C* and P* may be same or different and indicates S or R, is obtained by sulfonating a compound represented by the following general formula (5')

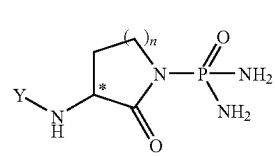

(5')

where n and Y are as described above; and the configuration at C* indicates S or R, by sulfur trioxide, reacting the resulting compound represented by the general formula (7) with an optically active amine represented by (1R,2S)-(−)-2-amino-1,2-diphenylethanol without isolating it, and resolving the formed diastereomeric salt with a fractional crystallization process.

17. The preparation method according to any one of claims 1, 7, 8 and 16, wherein optically active sulphostin or analogue thereof represented by the following general formula (1)

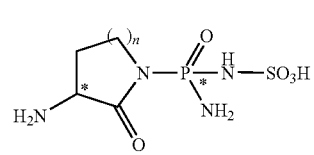

(1)

where n is an integer of 0 to 3; each configuration at C* and P* may be the same or different and indicates S or R, is obtained by reacting a compound represented by the following general formula (3')

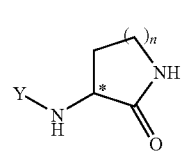

(3')

where n is an integer of 1 to 3, Y represents a protecting group for the amino group; and the configuration at C* indicates S or R, sequentially with a sililating agent, with a phosphorus oxyhalide represented by the general formula (4)

$$P(=O)T_3 \qquad (4)$$

where T represents a halogen atom, and further with ammonia; sulfonating the resulting compound represented by the following general formula (5')

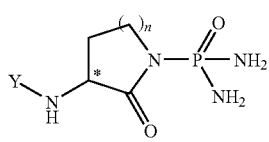
(5')

where n is an integer of 0 to 3, Y and C* are as described above), with sulfur trioxide; reacting the resulting compound represented by the general formula (7)

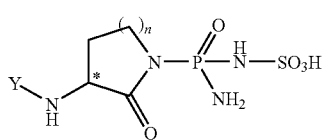
(7)

with an optically active amine represented by (1R,2S)-(−)-2-amino-1,2-diphenylethanol or (1S,2R)-(+)-2-amino-1,2-diphenylethanol, without isolating it; resolving the form diastereomeric salt with a fractional crystallization process to obtain an optically active amine salt of the optically active substance represented by the following general formula (8)

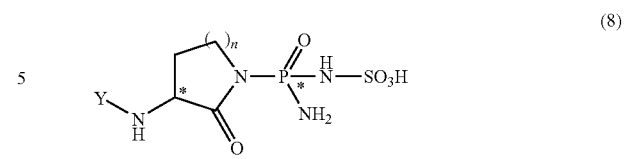
(8)

where n and Y are as described above; and C* and P* have the same meanings as above); and then removing the protecting group for the amino group and the optically active amine with a conventional process.

18. A salt of the compound of formula (8) formed by reaction of an optically active compound represented by the following general formula (8)

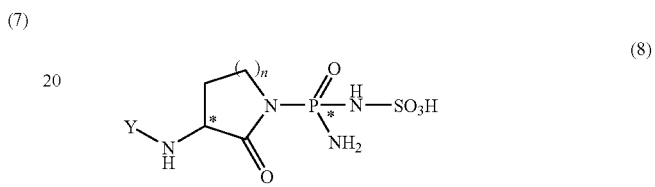
(8)

where n is an integer of 0 to 3; Y represents a protecting group for the amino group; and each configuration at C* and P* may be the same or different and indicates S or R, with an optically active amine represented by (1R,2S)-(−)-2-amino-1,2-diphenylethanol or (1S,2R)-(+)-2-amino-1,2-diphenylethanol.

* * * * *